united States Patent [19]
Sauvage et al.

[11] Patent Number: 5,401,730
[45] Date of Patent: Mar. 28, 1995

[54] METHOD FOR REDUCING PLATELET AGGREGATION

[75] Inventors: Lester R. Sauvage, Seattle; Svetlana Kaplan; Alexander Kaplan, both of Mountlake Terrace, all of Wash.

[73] Assignee: The Hope Heart Institute, Seattle, Wash.

[21] Appl. No.: 52,219

[22] Filed: Apr. 22, 1993

Related U.S. Application Data

[63] Continuation of Ser. No. 794,797, Nov. 19, 1991, abandoned, which is a continuation of Ser. No. 549,375, Jul. 6, 1990, abandoned.

[51] Int. Cl.$^6$ .................. A61K 31/60; A61K 31/315; A61K 31/19
[52] U.S. Cl. .................................. 514/165; 514/494; 514/557; 514/822
[58] Field of Search ............... 514/159, 101, 103, 822, 514/276, 165, 494, 557

[56] References Cited

U.S. PATENT DOCUMENTS

| | | | |
|---|---|---|---|
| 3,842,169 | 10/1974 | Schneyer | 514/161 |
| 4,080,446 | 3/1978 | Leopold et al. | 514/161 |
| 4,080,447 | 3/1978 | Amselem | 514/161 |
| 4,734,405 | 3/1988 | Koenig | 514/161 |

OTHER PUBLICATIONS

The Merck Index, abstracts Nos. 863 and 2297.
Handbook of Nonprescription Drugs, p. 129.
Bekheet, I. A., "The Effect of Some Inhibitors on the Activity of Lipoxygenase", Alex. Sci. Exch. 7(3):389–398, 1986.
Von S. Drescher, "On the Inhibitory Effect of Metal Salts on Experimental Vascular Calcinosis", Beitr. path. Anat. 130:74–92, 1969.
Greaves, M. W. and A. W. Skillen, "Effects of Long-Continued Ingestion of Zinc Sulphate in Patents with Venous Leg Ulceration", The Lancet, Oct. 31, 1970, 889–891, 1970.
Kaplan, S. et al., "A New Combination Therapy for Selective and Prolonged Antiplatelet Effect: Results in the Dog", Stroke 17(3):450–454, 1986.
Kaplan, S. et al., "The effect of Predetermined thrombotic potential of the recipient on small–caliber graft performance", J. Vasc. Surg. 3(2):311–321, 1986.
McBean, L. D. et al., "Serum Zinc and Alpha$_2$–Macroglobulin Concentration in Myocardial Infarction, Decubitus Ulcer, Multiple Myeloma, Prostatic Carcinoma, Down's Syncrome and Nephrotic Syndrome", Clinica Chimica Acta 50:43–51, 1974.
Weiss, H. J. et al., "Effect of Aspirin and Dipyridamole on the Interaction of Human Platelets with Sub–Endothelium: Studies Using Citrated and Native Blood", Thrombosis and Haemostasis 45(2):136–141, 1981.
Kannel, W. B. et al., "Fibrinogen and Risk of Cardiovascular Disease", JAMA 258(9):1183–1186, 1987.
Stone, M. C. and J. M. Thorp, "Plasma fibrinogen—a major coronary risk factor", J. Roy. Coll. Gen. Pract. 35(281), 565–569, 1985.
Wilhelmsen, L. et al., "Fibrinogen as a Risk Factor for Stroke and Myocardial Infarction", N. Engl. J. Med. 311(8):501–505, 1984.
Apprill, P. G. et al., "Ancrod decreases the frequency of cyclic flow variations and causes thrombolysis following acute coronary thrombosis", Amer. Heart J. 113(4):898–906, 1986.
Hossmann, V. et al., "Controlled Trail of Ancrod in Ischemic Stroke", Arch. Neurol. 40:803–808, 1983.

Primary Examiner—Raymond Henley, III
Assistant Examiner—K. Weddington
Attorney, Agent, or Firm—Christensen, O'Connor, Johnson & Kindness

[57] ABSTRACT

Patients having a predisposition for thrombus formation are effectively treated with compositions of acetylsalicylic acid, citric acid, thiamine and/or a zinc salt. The combination of aspirin and citric acid has been found to be significantly more effective in inhibiting platelet aggregability than aspirin alone, and thiamine contributes to the reduction in thrombotic potential by reducing plasma fibrinogen levels. Accordingly, new methods and compositions are disclosed for reducing the thrombotic potential of human or animal subjects, such as in the prophylaxis or treatment of atherosclerosis, vascular surgery patients or other cardiovascular diseases.

5 Claims, 2 Drawing Sheets

METHOD FOR REDUCING PLATELET AGGREGATION

This application is a continuation application based on application Ser. No. 07/794,797, filed on Nov. 19, 1991, now abandoned, which is a continuation application based on application Ser. No. 07/549,375, filed on Jul. 6, 1990, now abandoned.

FIELD OF THE INVENTION

This invention relates to methods and compositions for the treatment or prophylaxis of thrombosis. More particularly, this invention provides methods and compositions for reducing platelet aggregation and fibrinogen levels in circulating blood of a patient.

BACKGROUND OF THE INVENTION

At least half of the victims of cardiovascular disease (CVD) are asymptomatic until the occurrence of a major vascular obstruction. Thrombus formation frequently results in the loss of peripheral blood circulation, endangering limb viability, and potentially in the loss of life. The risk of thrombus obstruction is particularly pronounced after blood vessel surgery, where thrombus formation and vascular occlusion are relatively common.

Thrombus formation involves a complex interaction of aggregated platelets and activated coagulation factors with the damaged vessel wall. Circulating platelets are nonadherent to normal endothelium or to each other, but when the endothelial lining of a vessel is broken, the platelets adhere to exposed subendothelial collagen. This is the first step in the formation of hemostatic plugs, and requires participation of a protein made by endothelial cells called the von Willebrand (vW) factor. The vW factor is found both in the vessel wall and in plasma, and binds during platelet adhesion to a receptor present on a glycoprotein of the platelet surface membrane. Next, platelets are activated in reactions initiated by collagen and by thrombin formed at the injury site. These stimuli activate phospholipase C, an enzyme that hydrolyzes the membrane phospholipid, phosphatidyl inositol triphosphate. Products of this reaction activate protein kinase C and also increase the calcium concentration of platelet cytosol. As a result, a series of progressive, overlapping events ensue. The platelets change shape and develop long pseudopods. A receptor is assembled on the platelet surface membrane, and fibrinogen and other adhesive proteins bind to this receptor causing platelets to stick to each other. Arachidonic acid is liberated from membrane phospholipids and undergoes oxidation to products that include prostaglandin $H_2$ ($PGH_2$), which serves as an important cofactor for collagen-induced platelet activation, and thromboxane $A_2$ ($TxA_2$), which can act itself as an additional platelet activator. The contents of platelets are secreted, including adenosine diphosphate (ADP) which can also stimulate platelet activation and recruit new platelets into the growing hemostatic plug.

Subsequent to platelet aggregation, fibrinogen in the circulating blood is converted to fibrin to physically tie the hemostatic platelet plug in place. The platelet surface undergoes a reorganization that exposes procoagulant phospholipids needed for enzyme/cofactor complexes of blood coagulation to form on the platelet surface. Secretion of platelet factor V from platelet s-granules provides a key component for one of the enzyme/cofactor complexes. As a result, thrombin is generated in increasing amounts on the platelet surface, and converts fibrinogen into fibrin with the formation of fibrin strands that radiate outward from aggregated platelets helping to secure the platelet plug to the site of injury. Additionally, a mechanism within the platelets is activated which results in contraction of platelet actinomycin. This compresses and consolidates the platelet plug, further securing it to the site of injury.

In the in vivo regulation of thrombus formation, platelet aggregation is mediated by the $PGH_2$ derivative prostacyclin ($PGI_2$). Prostacyclin is also a vasodilator and is believed to render the vessel lining inert to platelet interactions. Thus, $TxA_2$ and $PGI_2$ have opposing effects on platelet aggregation, and the degree of the physiological effect of each in the cardiovascular system on the regulation of thrombus formation is determined mainly by their quantitative balance (Bush, H. L., Jr. et al., "Favorable Balance of Prostacyclin and Thromboxane $A_2$ Improves Early Patency of Human In Situ Vein Grafts," *J. Vasc. Surg.* 1:149–159, 1984; Coker, S. J. et al., "Thromboxane and Prostacyclin Release From Ischemic Myocardium In Relation To Arrhythmias," *Nature* 291:323–334, 1981; Hunter, G. C. et al., "Arterial Wall Thromboxane: Dominance After Surgery Predisposes to Thrombosis," *J. Vasc. Surg.* 1:314–319, 1984; and Zmuda, A., et al., "Experimental Atherosclerosis in Rabbits: Platelet Aggregation, Thromboxane $A_2$ Generation and Antiaggregatory Potency of Prostacyclin," *Prostaglandins* 14:1035, 1977).

Therapeutic treatments to alter thrombus formation have focused mainly on inhibition of the aggregation response. The most widely accepted agent for this purpose is acetylsalicylic acid (ASA), or aspirin. In the arachidonic acid cascade, aspirin acts as a cyclooxygenase inhibitor, blocking the conversion of arachidonic acid to the $PGH_2$ precursor prostaglandin $G_2$ ($PGG_2$). Since $PGG_2$ is a precursor to both $TxA_2$ and $PGI_2$, aspirin blocks both the aggregation inducing and aggregation inhibiting effects of these factors, respectively. As an antithrombotic agent, aspirin has had varying degrees of success. Although minimal amounts of aspirin are required for platelet inhibition, most of the clinical experience relates to relatively large doses. The nonselective, potent inhibition of high-dose aspirin on both $TxA_2$ and $PGI_2$ has caused investigators to consider the theoretical advantage of the use of low-dose therapy. Preferred inhibition of proaggregatory $TxA_2$ in humans has been limited to single-dose aspirin administration or short-term cumulative effect. It has been further found that the degree and duration of aspirin's beneficial effect is highly dependent on each subject's inherent thrombotic potential (see Zammit, M. et al., "Aspirin Therapy in Small Caliber Arterial Prostheses; Long Term Experimental Observations," *J. Vasc. Surg.* 1(6):839–851, 1984). For many individuals, aspirin has little or no discernable antiaggregatory activity, and is not effective in reducing a predisposition for thrombus formation.

To overcome some of the problems associated with aspirin therapy, it has been previously proposed to utilize certain thromboxane synthetase inhibitors (TSIs), which inhibit the formation of proaggregatory $TxA_2$ without interfering with the formation of antiaggregatory $PGI_2$. Various imidazole derivatives have been proposed for this purpose, for use either alone or in connection with low dose aspirin therapy. See, for example, Kaplan, S. et al., "A New Combination Therapy for Selective and Prolonged Antiplatelet Effect: Results in the Dog," *Stroke* 17:450–454 (1986). It has also been suggested that zinc ions exhibit an inhibitory activity toward collagen-induced platelet aggregation and serotonin release in vitro (Chapvil, M. et al., "Inhibitory Effect of Zinc Ions on Platelet Aggregation and Serotonin Release Reaction," *Life Sciences* (16):561–572, 1975) and toward platelet activating factor (PAF) in vitro (*Arch. Biochem. Biophys.* 272(2):466–475 (1989); *Arch. Biochem. Biophys.* 260(2):841–846, 1988), and that hydroxyurea, citric acid and ascorbic acid inhibit plant lipoxygenase activity in vitro (Bekheet, I.A. et al., "The Effect of Some Inhibitors on the Activity of Lipoxygenase," *Alex. Sci. Exch.* 7(3):389–398, 1986).

Other therapeutic treatments to alter thrombus formation have involved a reduction in fibrinogen levels, since fibrinogen levels have been shown to be significantly related to cardiovascular risk factors, including blood viscosity, coagulation and fibrinolysis (see Kannel, W. B. et al., "Fibrinogen and Risk of Cardiovascular Disease —The Framingham Study," *JAMA* 258 (9):1183–1186, 1987; Wilhelmsen, L. et al., "Fibrinogen as a Risk Factor for Stroke and Myocardial Infarction," *N. Eng. J. Med.* 311 (8):501–504 (1984); and Stone, M. C. et al., "Plasma Fibrinogen —a Major Coronary Risk Factor," *J. Roy. Col. Gen Prac.* 35: 565–569, December, 1985).

Plasminogen activators, such as streptokinase and tissue plasminogen activator, directly reduce systemic fibrinogen levels and have been administered by intracoronary, intravenous and/or intramuscular injection for the acute phase treatment of coronary disorders, such as ischemic stroke and coronary thrombosis. In addition, fibrinogen degrading agents such as ancrod, a viper venom enzyme isolated from *Agkistrodon rhodostoma*, the Malaysian pit viper, have been shown to have anticoagulative and thrombolytic activity when administered by intravenous infusion (see, for example, Hossman, V. et al., "Controlled Trial of Ancrod in Ischemic Stroke," *Arch. Neurol.* 40:804–808, 1983; and Apprill, P. G., et al., "Ancrod Decreases the Frequency of Cyclic Flow Variations and Causes Thrombolysis Following Acute Coronary Thrombosis," *Am. Heart J.* 113(4):898–906, 1987). While plasminogen activators and ancrod have been shown to have some degree of efficacy when administered IV or IM in the acute phase treatment of thrombotic disorders, they are inappropriate for long term, routine administration in the chronic prophylaxis or treatment of cardiovascular disease.

SUMMARY OF THE INVENTION

It has now been found that patients having a predisposition for thrombus formation can be effectively treated with compositions comprising aspirin, citric acid, and thiamine, and optionally a pharmaceutically acceptable zinc salt. The combination of aspirin and citric acid has been found to be significantly more effective in inhibiting platelet aggregability than aspirin alone, while thiamine contributes to the reduction in thrombotic potential by reducing plasma fibrinogen levels. Accordingly, new methods and compositions are disclosed for reducing the blood thrombotic potential of human or animal subjects. The new methods and compositions are highly effective in the treatment of cardiovascular patients, such as in the prophylaxis or treatment of atherosclerosis, vascular surgery patients or other cardiovascular diseases.

DESCRIPTION OF THE PREFERRED EMBODIMENTS

Figure 1:
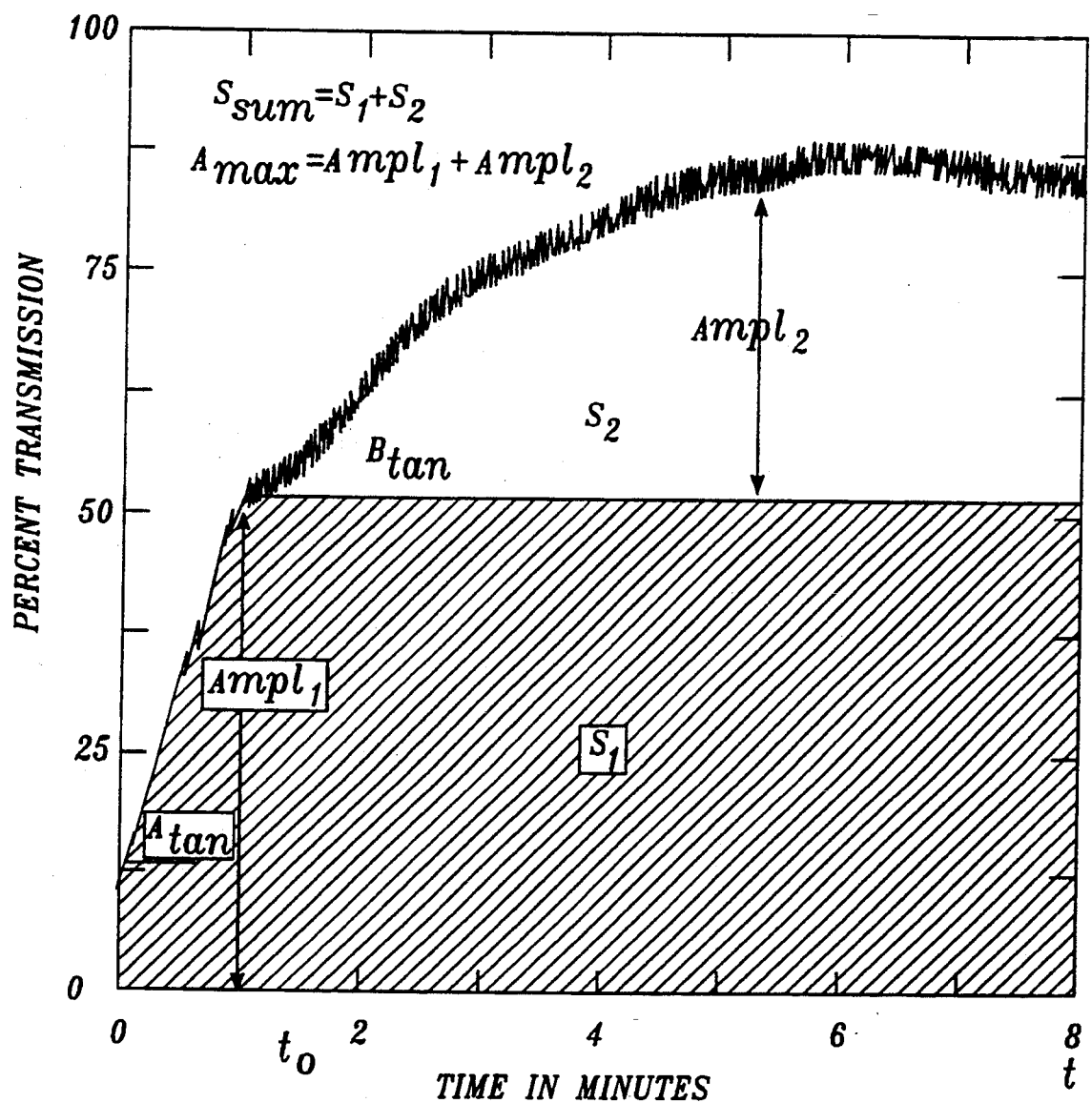
FIG. 1 is a graph of a representative adenosine diphosphate (ADP)-induced platelet aggregation response showing the percent transmission of platelet rich plasma (PRP) as a function of time after induction of aggregation.

In accordance with the present invention, it has been found that therapeutic compositions comprising aspirin and citric acid are significantly more effective for reducing platelet activity than aspirin alone. In addition, it has been observed that compositions comprising thiamine are effective for reducing fibrinogen levels. Accordingly, one aspect of the present invention provides a method for reducing a predisposition for thrombus formation in a patient comprising administering to the patient a therapeutically effective amount of a composition comprising aspirin and citric acid. In another aspect of the invention, a predisposition for thrombus formation in a patient is treated by administering to the patient a therapeutically effective amount of a composition comprising thiamine. In one particularly preferred embodiment, a patient is treated by administering to the patient amounts of aspirin, citric acid, thiamine and a zinc salt effective to reduce platelet aggregation and fibrinogen levels in the blood of the patient, thereby decreasing the likelihood of thrombus formation by at least partially blocking both the platelet aggregation and fibrin formation pathways.

Other aspects of the invention provide therapeutic compositions comprising an amount of aspirin and citric acid effective to reduce platelet aggregation when administered to a patient and/or an amount of thiamine effective to reduce fibrinogen levels in the blood of a patient. In a particularly preferred embodiment, the compositions of the invention comprise aspirin, citric acid, thiamine and a zinc salt.

The methods and compositions of the invention may be used prophylactically or therapeutically in the treatment of patients who are at high risk of thrombus formation, such as in the treatment of atherosclerosis, vascular surgery patients, and patients with other types of cardiovascular disease.

In accordance with one aspect of the present invention, amounts of acetylsalicylic acid and citric acid effective to reduce platelet aggregation are administered to the patient. Effective but nontoxic amounts of acetylsalicylic acid and citric acid may be readily determined by the ordinary skilled physician. The precise amounts required for this purpose will depend upon the body weight of the patient, physiological condition of the patient, thrombotic potential of the patient, desired effect, and other factors. However, for most purposes, at least about 0.5 mg of acetylsalicylic acid per kg of body weight of the patient per day, more preferably from about 2 to about 4 mg of acetylsalicylic acid per kg of body weight of the patient per day, and at least about 0.5 mg of citric acid per kg of body weight of the patient per day, more preferably from about 2 to about 4 mg of citric acid per kg of body weight of the patient per day is administered to the patient.

In accordance with another aspect of the invention, amounts of thiamine effective to reduce fibrinogen levels are administered to the patient. The normal fibrinogen levels in human subjects is dependent upon diet, climate, altitude and other factors, but commonly ranges from about 200 to about 400 mg/dl of plasma. With certain disease states, however, the fibrinogen level of a patient can be higher. In the practice of the invention, individual dosages of thiamine may be determined for each patient, and are preferably designed to reduce fibrinogen levels in the patient plasma to less than about 350 mg/dl, more preferably less than about 300 mg/dl. Again, the precise amounts to be administered will depend on many factors. However, for most purposes, at least about 0.05 mg of thiamine per kg of body weight of the patient per day is administered to the patient, more preferably from about 0.075 to about 1.25 mg thiamine per kg of body weight of the patient per day of is administered to the patient.

In yet another aspect, a patient is treated in accordance with the foregoing and by additionally administering to the patient an amount of a pharmaceutically acceptable zinc salt effective to result in a reduction in platelet aggregability of the patient. In most cases, at least about 0.01 mg of the zinc salt per kg of body weight of the patient per day will be effective for this purpose, but significantly larger doses may be employed, if desired. Suitable zinc salts include, for example, the pharmaceutically acceptable acid addition salts of $Zn^{2+}$, such as the hydrochloric, sulfuric, phosphoric, acetic, citric, oxalic, malonic, salicylic, malic, gluconic, fumaric, succinic, ascorbic, maleic, methanesulfonic, arginine or similar pharmaceutically acceptable salts. Presently particularly preferred salts include zinc acetate and zinc sulfate.

In another aspect of the invention, compositions are provided which comprise amounts of acetylsalicylic acid and citric acid effective to reduce platelet aggregation, and an amount of thiamine effective to reduce fibrinogen levels when administered to a patient. In addition, the compositions of the invention may further comprise an amount of a pharmaceutically acceptable zinc salt effective to result in a reduction in platelet aggregability of the patient, as described above, as well as pharmaceutically acceptable carriers. Preferred compositions of the invention are designed for unit dosage administration, such as, for example, for routine one dose a day administration, and may contain representative amounts of the active compounds within the following ranges:

| Component | Amount (mg/dose) |
|---|---|
| acetylsalicylic acid | 50–650 |
| citric acid | 50–650 |
| thiamine | 2–100 |
| zinc salt | 0–100 |

In a presently particularly preferred illustrative embodiment for oral administration, compositions of the invention comprise from about 100 to about 200 mg/dose of acetylsalicylic acid, from about 100 to about 200 mg/dose of citric acid, from about 5 to about 10 mg/dose of thiamine and from about 0.5 to about 2 mg/dose of a pharmaceutically acceptable zinc salt.

The compositions of the invention can be administered in any effective pharmaceutically acceptable form to warm blooded animals, e.g., in oral, parenteral or infusable dosage forms, in transdermal formulations or as a buccal or nasal spray. Suitable parenteral routes of administration include, for example, intramuscular, intravenous, intraperitoneal or subcutaneous administration of the compounds. For most purposes, oral administration will be preferred.

Solid dosage forms for oral administration include capsules, tablets, pills, powders and granules. In such solid dosage forms, the active compounds may be admixed with at least one inert diluent such as sucrose, lactose or starch. Such dosage forms may also comprise, as is normal practice, additional substances other than inert diluents, e.g., lubricating agents such as magnesium stearate. In the case of capsules, tablets and pills, the dosage forms may also comprise buffering agents. Tablets and pills may additionally be prepared with enteric coatings.

Liquid dosage forms for oral administration include pharmaceutically acceptable emulsions, solutions, suspensions, syrups and elixirs containing inert diluents commonly used in the art, such as water. Besides such inert diluents, compositions of the may also comprise adjuvants such as wetting agents, emulsifying and suspending agents, and sweetening, flavoring and perfuming agents.

In addition to the active compounds, compositions according to the invention for parenteral injection may comprise pharmaceutically acceptable sterile aqueous or nonaqueous solutions, suspensions or emulsions. Examples of suitable nonaqueous carriers, diluents, solvents or vehicles include propylene glycol, polyethylene glycol, vegetable oils, such as olive oil, and injectable organic esters, such as ethyl oleate. Such compositions may also contain adjuvants, such as preserving, wetting, emulsifying and dispersing agents. They may be sterilized, for example, by filtration through a bacteria-retaining filter, or by incorporating sterilizing agents in to the compositions. They can also be manufactured in the form of sterile solid compositions which can be dissolved in sterile water, or other sterile injectable medium, immediately before use.

The foregoing may be better understood in connection with the following examples, which are presented for purposes of illustration and not by way of limitation.

EXAMPLES

As used in the following examples, platelet aggregations were performed on a Payton dual channel aggregometer with an Omniscribe B-5000 chart recorder with platelet rich plasma (PRP) prepared from venous blood anticoagulated with 3.8% sodium citrate according to the turbidometric method of Born, GVR, "Aggregation of Blood Platelets by Adenosine Diphosphate and Its Reversal," *Nature* 194:927–929, 1962. Platelet aggregations were induced with adenosine diphosphate (ADP). It has been previously shown that the rate and persistence of platelet aggregation in response to adenosine diphosphate can be used as a measure of the thrombotic potential of blood (see, Kaplan, S., et al., "The effect of Predetermined Thrombotic Potential of the Recipient on Small-Caliber Graft Performance," *J. Vasc. Surg.* 3:311–321, 1986, the disclosure of which is incorporated herein by this reference). Using autologous platelet poor plasma (PPP), the platelet count in PRP was adjusted to 250,000 ±25,000 platelets/ml.

Following a three minute period at 37° C., ADP was added to the PRP to a final concentration of 2.5μM, and the change in aggregation response was assessed by degree of inhibition as represented by alteration of the aggregation curve. Referring to FIG. 1 (a typical adenosine diphosphate-induced platelet aggregation curve depicting percent transmission (% Tran) as a function of time), platelet aggregability ($K_{agg}$) was determined by the following equation (1):

$$K_{agg} = \frac{A_{max} \times S_1}{S_{sum} \times S_{test}} \times P_c$$

where $A_{max}$ is the maximum amplitude of the aggregation curve, $S_1$ is the primary aggregation area (see FIG. 1), $S_2$ is the secondary aggregation area, $S_{sum}$ is the total aggregation area (i.e., $S_1 + S_2$), $S_{test}$ is a normalization parameter equal to 64 units$^2$ and $P_c$ is the whole blood platelet count $\times 10^{-3}$.

Plasma fibrinogen levels were measured by clotting assay using the method of Clauss (Clauss, A., "Gerinnungsphysiologische Schneliomethode zur Bestimmung des Fibrinogens," *Acta Haemat.* 17:237, 1957).

Example 1

Sixteen human patients shown to have an inadequate platelet aggregation response to aspirin administration alone, were given daily doses of a composition having the following formulation:

| | |
|---|---|
| aspirin | 158 mg |
| citric acid | 158 mg |
| thiamine hydrochloride | 8 mg |
| zinc acetate | 1 mg |
| Total per dose | 325 mg |

The $K_{agg}$ and fibrinogen level (expressed in mg/dl) of each patient was determined prior to treatment with any medication (No Med) and/or after aspirin treatment alone (ASA), and then again after varying periods of daily administration of a single dose of the composition set forth above (Post Treatment). The results are shown in the following Table 1:

TABLE 1

| | $K_{agg}$ | | | Fibrinogen | |
|---|---|---|---|---|---|
| ID | NM | ASA | PT | BL | PT |
| 1 | nd | 17.24 | 9.34 | 355 | 280 |
| 2 | nd | 11.81 | 8.90 | 400 | 335 |
| 3 | nd | 14.44 | 8.44 | 513 | 280 |
| 4 | nd | 9.76 | 6.27 | 515 | 375 |
| 5 | nd | 20.18 | 12.30 | 370 | 338 |
| 6 | nd | 10.31 | 11.11 | 420 | 335 |
| 7 | nd | 5.37 | 3.33 | 420 | 305 |
| 8 | 16.67 | 16.60 | 8.3 | 335 | 305 |
| 9 | nd | 6.22 | 3.11 | 370 | 305 |
| 10 | nd | 7.33 | 6.04 | 410 | 280 |
| 11 | nd | 11.51 | 6.75 | 390 | 305 |
| 12 | nd | 11.38 | 6.50 | 390 | 270 |
| 13 | 24.17 | 11.20 | 8.96 | 352 | 280 |
| 14 | 17.87 | 11.92 | 11.42 | 370 | 290 |
| 15 | nd | 24.76 | 13.68 | 355 | 255 |
| 16 | nd | 3.90 | 3.25 | 480 | 307 |
| MV | 19.57 ± 4.03 | 12.12 ± 5.53 | 7.98 ± 3.21 | 402.81 ± 55.76 | 302.8 ± 30.73 |

NM = no medication
ASA = aspirin alone
PT = post treatment
BL = baseline (pretreatment)
nd = not determined
MV = mean value As can be seen from Table 1, the administration of aspirin (ASA) alone results in a partial reduction in platelet aggregation ($K_{agg}$) in humans, as is known in the art. However, the daily administration of a representative composition of the invention unexpectedly results in a further substantial reduction in platelet aggregation over that elicited by aspirin alone, as well as a substantial reduction in fibrinogen levels.

Example 2

Figure 2:
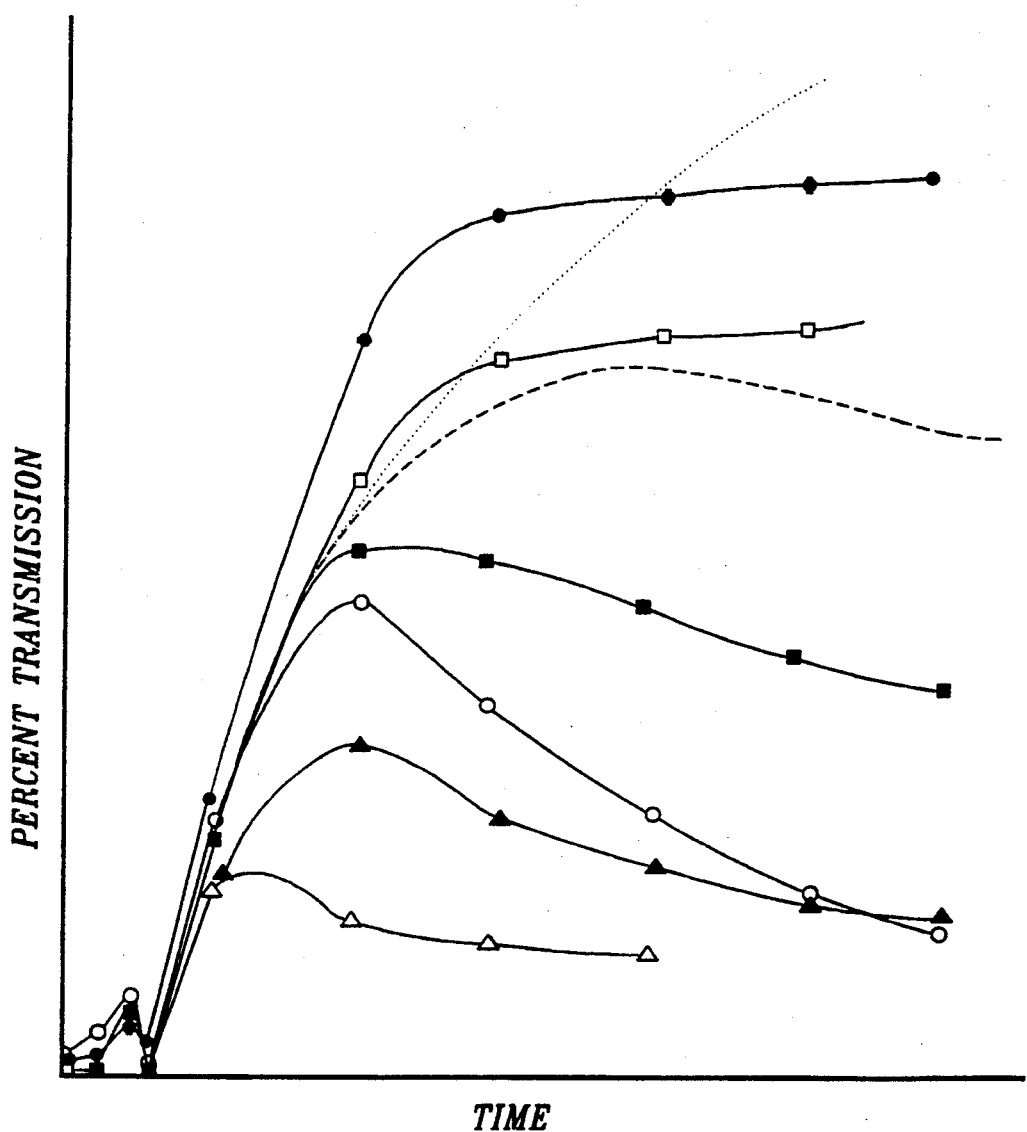
FIG. 2 is a graph of the ADP-induced platelet aggregation response of PRP with no treatment (baseline, represented by solid dots), and after exposure to sodium citrate (open squares), aspirin and sodium citrate (closed squares), aspirin alone (open circles), citric acid (closed triangles), aspirin and citric acid (open triangles), water alone (dotted line) or water and ethanol (dashed line).

To demonstrate the effect of various components on platelet aggregation in vitro, six identical samples of platelet rich plasma (PRP) from dog blood were treated with the components described below, induced with a final concentration of 10 μM ADP and tested for platelet aggregation response, as described above. The results are shown in platelet aggregation curves of FIG. 2, in which the baseline (no medication control) is represented by solid dots, PRP treated with 2.5 mMol aspirin in ethanol is represented by open circles; PRP treated with 10 mMol of sodium citrate alone is represented by open squares, PRP treated with 2.7 mMol aspirin and 10 mMol sodium citrate in ethanol and water, respectively, is represented by closed squares; PRP treated with 10 mMol citric acid alone is represented by closed triangles, PRP treated with 2.7 mMol aspirin and 10 mMol citric acid in ethanol and water, respectively, is represented by open triangles; and controls with PRP treated by 10 μL of water or 10 μL water and 2.5 μL ethanol are represented by a dotted or dashed line, respectively. As can be seen in FIG. 2, the combined inhibitory effect of aspirin and citric acid is substantially greater than that of each component separately, or that of aspirin combined with sodium citrate.

Example 3

Fifty mg of thiamine were administered orally to each of five healthy human subjects on a daily basis for a period of two weeks. The plasma fibrinogen levels of each subject both before and at the end of the treatment period are shown in the following Table 2:

TABLE 2

| Subject # | Initial Fibrinogen Level mg/dl | Fibrinogen After 2 Weeks of Thiamine Administration | |
|---|---|---|---|
| | | Level (mg/dl) | % Reduction |
| 1 | 235 | 173 | 26.4 |
| 2 | 255 | 200 | 21.6 |
| 3 | 255 | 195 | 23.6 |
| 4 | 335 | 280 | 16.4 |
| 5 | 315 | 245 | 22.2 |
| Mean Value | 279 | 218 | 22.04 |
| St. Deviat. | 43.36 | 43.15 | 3.66 |

As shown in Table 2, the daily administration of thiamine resulted in a substantial reduction in the fibrinogen level of each patient, and in an average 22% reduction in fibrinogen levels of all of the subjects studied.

Example 4

The procedure of Example 3 was repeated substituting 158 mg of citric acid per day for the thiamine in four healthy human subjects. The results are shown in the following Table 3:

TABLE 3

| Subject # | Initial Fibrinogen Level mg/dl | Fibrinogen After 2 Weeks of Thiamine Administration | |
|---|---|---|---|
| | | Level (mg/dl) | % Deviation |
| 1 | 280 | 260 | −7% |
| 2 | 248 | 220 | −11.3% |

TABLE 3-continued

| Subject # | Initial Fibrinogen Level mg/dl | Fibrinogen After 2 Weeks of Thiamine Administration | |
| --- | --- | --- | --- |
| | | Level (mg/dl) | % Deviation |
| 3 | 223 | 230 | +3.14% |
| 4 | 232 | 238 | +2.6% |
| Mean Value | 245.7 | 237 | 3.14 |
| St. Deviat. | 25 | 17 | 7.16 |

As can be seen from Table 3, there is no significant correlation between citric acid administration and fibrinogen levels of the subjects studied.

Example 5

The procedure of Example 3 was repeated substituting 158 mg of aspirin per day for the thiamine in four healthy human subjects. The results are shown in the following Table 4:

TABLE 4

| Subject # | Initial Fibrinogen Level mg/dl | Fibrinogen After 2 Weeks of Thiamine Administration | |
| --- | --- | --- | --- |
| | | Level (mg/dl) | % Deviation |
| 1 | 215 | 240 | +11.6% |
| 2 | 248 | 238 | −4.0% |
| 3 | 247 | 265 | +7.3% |
| 4 | 205 | 180 | −12.2% |
| Mean Value | 228.8 | 230.8 | 0.7% |
| St. Deviat. | 22.2 | 40 | 10.8 |

As can be seen from Table 4, there is no significant correlation between aspirin administration and fibrinogen levels in the subjects studied.

Example 6

Six human patients were selected for treatment after experiencing one or more occurrences of thrombotic vascular occlusion following vascular surgery. The thrombotic condition of each subject was clinically determined to be inadequately controlled by conventional aspirin therapy. Each of the six subjects was judged to be at high risk of subsequent vascular occlusions, and of significant potential for loss of life or limb. Each subject was placed on a daily treatment regimen of a single dose of the composition of Example 1. All of the subjects were routinely examined, and have remained free from clinically observable thrombotic occlusions since beginning the treatment regimen, for periods extending from two months to over 12 months. Each subject remains free from complications associated with their prior symptoms, and has been judged to have avoided significant hospitalization and medical care which would have otherwise been required.

The therapeutic effects of the practice of the invention in most human and animal subjects have included a dramatic inhibition of platelet aggregation and decrease in fibrinogen levels, together with a resulting substantial decrease or elimination of thrombotic occlusion events. The inhibitory action of the compositions of the invention on platelet activity has been shown to be much more effective than that elicited by aspirin alone. In addition, the subjective clinical experience in patients treated according to the invention has been highly favorable as judged by lack of symptoms, a relative freedom from complications and an overall higher quality of life, which is in marked contrast to their pretreatment state. The methods and compositions of the invention therefore provide a safe, effective means for the long-term, on-going prophylactic or therapeutic treatment of patients having a predisposition for life threatening thrombus formation, where adequate chronic treatment has heretofore been unavailable.

Various modifications and applications of the methods and compositions of the invention will be apparent from the foregoing to those skilled in the art. Any such modifications and applications are intended to be within the scope of the appended claims except insofar as precluded by the prior art.

What is claimed is:

1. A method of treating a patient comprising administering to the patient a composition comprising at least about 0.5 mg of acetylsalicylic acid per kg of body weight of the patient per day, and at least about 0.5 mg of citric acid per kg of body weight of the patient per day, whereby the platelet aggregation of the patient is reduced more than if the patient had been treated with acetylsalicylic acid alone.

2. The method of claim 1 wherein from about 2 to about 4 mg of acetylsalicylic acid per kg of body weight of the patient per day is administered to the patient.

3. The method of claim 1 wherein from about 2 to about 4 mg of citric acid per kg of body weight of the patient per day is administered to the patient.

4. The method of claim 1 which further comprises administering to the patient an amount of a pharmaceutically acceptable zinc salt effective to reduce the platelet aggregation activity of the patient.

5. The method of claim 4 wherein at least about 0.01 mg of a pharmaceutically acceptable zinc salt per kg of body weight per day is administered to the patient.

* * * * *

UNITED STATES PATENT AND TRADEMARK OFFICE
CERTIFICATE OF CORRECTION

PATENT NO. : 5,401,730
DATED : March 28, 1995
INVENTOR(S) : L.R. Sauvage et al.

It is certified that error appears in the above-indentified patent and that said Letters Patent is hereby corrected as shown below:

Title page:[56]   Refs. Cited       "Lon-g-Continued" should read --Long-Continued--
                  Other Pubs
                  (Pub. No. 3)

Title page:[56]   Refs. Cited       "Trail" should read --Trial--
                  Other Pubs
                  (Pub. No. 12)

Col. 1, line 68,   "s-granules" should read --$\alpha$-granules--

Col. 6, line 68,   "platelets/mi." should read --platelets/ml.--

Signed and Sealed this

Thirteenth Day of June, 1995

Attest:

BRUCE LEHMAN

*Attesting Officer*   *Commissioner of Patents and Trademarks*